(12) United States Patent
Lubinski (10) Patent No.: US 10,327,862 B2
(45) Date of Patent: Jun. 25, 2019

(54) FIDUCIAL MARKER DEPLOYMENT SYSTEM

(71) Applicant: COVIDIEN LP, Mansfield, MA (US)

(72) Inventor: Alexander A. Lubinski, Rocklin, CA (US)

(73) Assignee: COVIDIEN LP, Mansfield, MA (US)

(*) Notice: Subject to any disclaimer, the term of this patent is extended or adjusted under 35 U.S.C. 154(b) by 434 days.

(21) Appl. No.: 14/845,569

(22) Filed: Sep. 4, 2015

(65) Prior Publication Data

US 2016/0074131 A1 Mar. 17, 2016

Related U.S. Application Data

(60) Provisional application No. 62/051,517, filed on Sep. 17, 2014.

(51) Int. Cl.
*A61B 6/00* (2006.01)
*A61B 90/00* (2016.01)
(Continued)

(52) U.S. Cl.
CPC .......... *A61B 90/39* (2016.02); *A61B 17/3468* (2013.01); *A61M 37/0069* (2013.01);
(Continued)

(58) Field of Classification Search
CPC ........ A61B 17/3468; A61B 2090/3908; A61B 2090/3925; A61B 2090/3954;
(Continued)

(56) References Cited

U.S. PATENT DOCUMENTS

| 4,498,482 A | 2/1985 | Williams |
| 5,279,570 A | 1/1994 | Dombrowski et al. |

(Continued)

FOREIGN PATENT DOCUMENTS

| CA | 1150580 | 7/1983 |
| EP | 1518549 A1 | 3/2005 |

(Continued)

OTHER PUBLICATIONS

Extended European Search Report for Application No. 15185396.7 from the European Patent Office dated Feb. 11, 2016.
(Continued)

*Primary Examiner* — Mark D Remaly (57) ABSTRACT

The present disclosure generally relates a fiducial marker deployment system configured for controlled deployment of at least one of a plurality of preloaded specially-configured fiducials in a controlled serial manner to a desired target site. The deployment system generally includes a deployment device configured to deploy at least one of a plurality of preloaded fiducials to a target site within a patient via a rotational deployment mechanism. Each fiducial generally includes a pellet-like body having a groove helically formed along an outer surface thereof and the deployment device includes a deployment catheter having an internally threaded lumen configured to engage the helical groove of each fiducial so as to allow rotational loading and deployment of each fiducial.

16 Claims, 6 Drawing Sheets

(51) Int. Cl.
  *A61B 17/34* (2006.01)
  *A61M 37/00* (2006.01)
(52) U.S. Cl.
  CPC .................. *A61B 2090/3908* (2016.02); *A61B 2090/3925* (2016.02); *A61B 2090/3954* (2016.02); *A61B 2090/3966* (2016.02); *A61B 2090/3987* (2016.02); *A61B 2090/3995* (2016.02)
(58) Field of Classification Search
  CPC .... A61B 2090/3966; A61B 2090/3987; A61B 2090/3995; A61B 90/39; A61M 37/0069
  See application file for complete search history.

(56) References Cited

U.S. PATENT DOCUMENTS

| | | | |
|---|---|---|---|
| 5,810,769 | A | 9/1998 | Schlegel et al. |
| 6,102,887 | A | 8/2000 | Altman |
| 2003/0199760 | A1 | 10/2003 | Curpen et al. |
| 2009/0209804 | A1 | 8/2009 | Seiler |
| 2009/0270797 | A1 | 10/2009 | Aubert et al. |
| 2009/0299384 | A1 | 12/2009 | Iida et al. |
| 2010/0331677 | A1 | 12/2010 | Hong et al. |
| 2014/0243844 | A1 | 8/2014 | Clancy |
| 2014/0371586 | A1 | 12/2014 | Ryan et al. |
| 2017/0135692 | A1* | 5/2017 | Belson ............... A61B 17/0057 |

FOREIGN PATENT DOCUMENTS

| | | | |
|---|---|---|---|
| EP | 1935373 | A2 | 6/2008 |
| EP | 2609872 | A2 | 7/2013 |
| JP | 2004267772 | A | 9/2004 |
| JP | 2007-512100 | | 5/2007 |
| JP | 2008521527 | A | 6/2008 |
| JP | 2010012212 | A | 1/2010 |
| JP | 2012061143 | A | 3/2012 |
| JP | 2012525215 | A | 10/2012 |
| JP | 2013514142 | A | 4/2013 |
| JP | 2015506761 | A | 3/2015 |
| WO | 0128631 | A1 | 4/2001 |
| WO | 2010126750 | A2 | 11/2010 |
| WO | 2011075380 | A1 | 6/2011 |
| WO | 2013116142 | A1 | 8/2013 |

OTHER PUBLICATIONS

Partial Search Report for Application No. 16192691.0 dated Mar. 15, 2017 from the European Patent Office.
Extended European search report for Application No. 16192691.0 from the European Patent Office dated Jul. 4, 2017.
English translation of Japanese Office action dated Sep. 20, 2017, for Patent Application No. 2016-197946, from the Japanese Patent Office.
Notice of Reasons for Rejection for Japanese Patent Application No. 2015-178809 dated Jul. 14, 2016, English translation.
Patent Examination Report No. 1 for Australian Application No. 2015224523, dated Apr. 21, 2016 from the Australian Government.
Examination Report for Canadian Application No. 2,904,700 from the Canadian intellectual Property dated Sep. 23, 2016.
Examiner's Report for Canadian Application No. 2,944,259 dated Feb. 2, 2018 from the Canadian Intellectual Property Office.
English translation of Chinese Office Action dated Jan. 17, 2018, for Patent Application No. 201510593299.0, from the Chinese Patent Office.
Examination Report for Australian Application No. 2018200018 dated Nov. 21, 2018 from IP Australian.
Jun. 1, 2018 Notice of Allowance for Japanese Application No. 2016-197946.

* cited by examiner

FIDUCIAL MARKER DEPLOYMENT SYSTEM

CROSS REFERENCE TO RELATED APPLICATION

The present application claims the benefit of and priority to U.S. Provisional Application Ser. No. 62/051,517, filed on Sep. 17, 2014, the entire contents of which are incorporated herein by reference.

FIELD OF THE INVENTION

The present disclosure generally relates to medical devices, and, more particularly, to a deployment device configured for deployment of specially-configured fiducial markers.

BACKGROUND

Medical procedures often require locating and treating target areas within a patient. In some procedures, it is important to locate the target with a high degree of precision to limit damaging healthy tissue surrounding the target. For example, it is particularly important to know or be able accurately to estimate the precise location of the target in radiation oncology because it is desirable to limit the exposure of adjacent body parts to the radiation in a patient already suffering the depredations of cancer. However, in all treatment procedures, whether radiologic or otherwise, it is most desirable to be able to accurately target a region to be treated in a manner that protects the tissue and organs immediately surrounding the target location.

In many applications, it is not possible to directly view a treatment target or portion thereof (such as, for example, a cancerous tumor, cyst, pseudocyst, or other target) that needs to be acted on in some manner (e.g., biopsy, excision, etc.). It is therefore highly advantageous to have some mechanism for permitting the target to be located accurately so that the procedure can be carried out in an accurate and precise manner while avoiding damage to healthy tissue.

Even for target regions that may be visualized using CAT (computer-assisted tomography) scans, MRI (magnetic resonance imaging), x-rays, ultrasound, or other techniques, difficulties often arise in targeting a treatment. This is particularly true for target regions within a torso of a patient and soft tissue regions. Due to the mobility of tissues in those regions (e.g., movement of internal organs during respiration and/or digestion, the movement of breast tissue with any change of body position, etc.), a target region may not remain fixed relative to anatomical landmarks and/or to marks that can be placed onto an external surface of a patient's body during one of those visualization procedures.

Several techniques have been developed to address this problem. One such technique is to place markers into the patient along the margins of the target region. The markers may be active (e.g., emitting a signal useful in targeting a therapy) or passive (e.g., fiducial markers) that can be used for targeting under ultrasound, MRI, x-ray, or other targeting techniques.

For the purposes of creating targets for medical imaging, fiducial markers (e.g., hereinafter referred to as "fiducials") are small implants that are placed within the body cavity and give medical imaging systems permanent or semi-permanent targets for imaging and diagnosis. A fiducial is generally formed of a radio-opaque material and placed adjacent to a target site so that the target can be effectively located and treated with a device that targets a site using the fiducials as positional markers under radiographic detection. The placement of more than a single fiducial is generally desirable, as it allows for imaging systems to more accurately determine the location of a specific tissue based on multiple fiducials surrounding the tissue, which results in a more accurate orientation of targeted visualization. For example, in some instances, the placement of three fiducials is desirable, as it allows for imaging systems to more accurately triangulate and determine the location of the specific tissue and provide a three-dimensional orientation of targeted visualization.

Generally, fiducials are placed and positioned within a patient's body via percutaneous placement procedures utilizing the traditional "stylet-push" method. The traditional stylet-push procedure generally consists of a catheter having an internal lumen, where one or more fiducials are loaded within. The fiducials are then pushed out of the catheter by advancing a stylet through the catheter lumen, thereby driving the fiducials out of a distal end the catheter and into the desired location.

Figure 1:
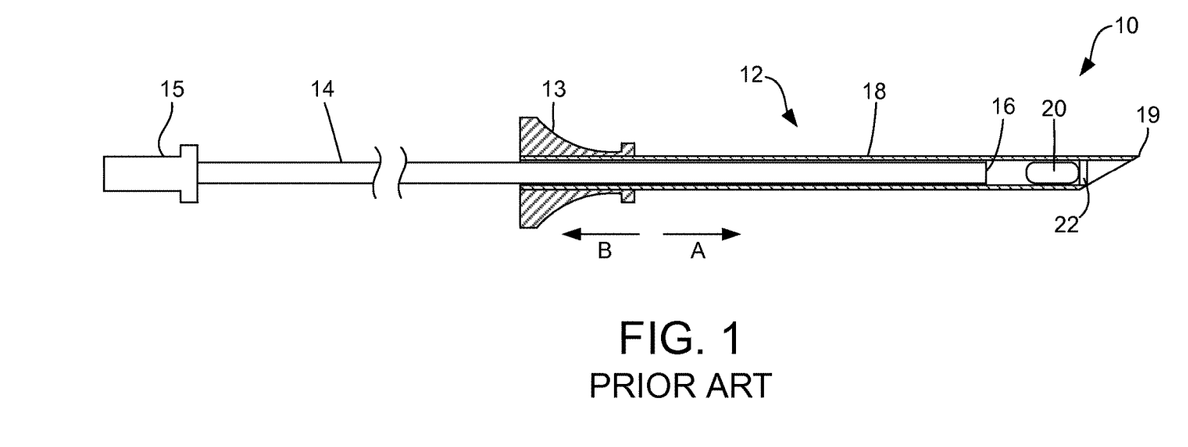
FIG. 1 is a cross-sectional view of an embodiment of a fiducial marker introducer known in the art.
Figure 2:
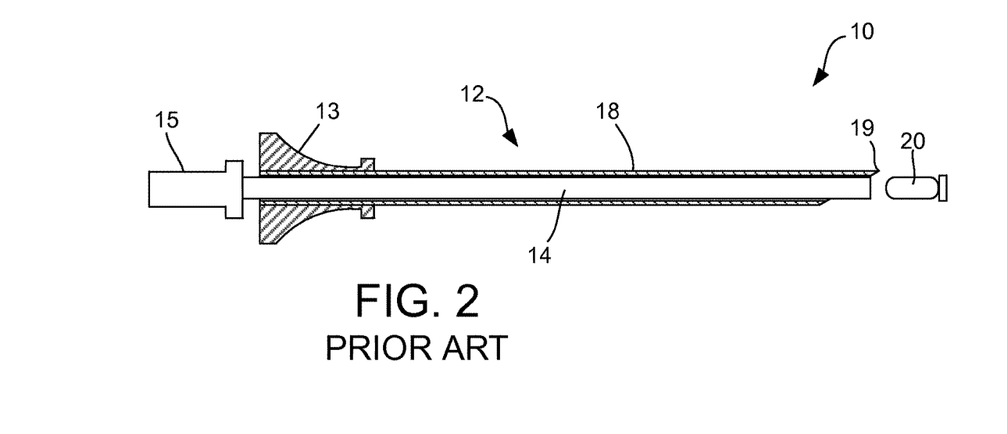
FIG. 2 is a cross-sectional view of the fiducial marker introducer of FIG. 1 illustrating advancement and of the fiducial via a traditional stylet-push method.

FIGS. 1 and 2 are provided to illustrate one embodiment a two-piece introducer 10 currently available for use in placement of fiducials via the stylet-push method. Referring FIG. 1, the introducer 10 includes a needle 12 and a stylet 14 slidably disposed within the needle 12. The stylet 14 includes a first handle 15 and a blunt distal end 16. The needle 12 includes a second handle 13 and a bevel-tipped cannula 18 extending through the second handle 13. The cannula 18 is configured to hold a fiducial 20 within. The cannula 18 has a distal tip 19 configured for percutaneous implantation of the fiducial 20 into the patient.

In a pre-loaded configuration, as shown in FIG. 1, the fiducial 20 may be retained within the cannula 18 by a plug 22 made from bone wax or other suitable bio-compatible material(s). This is typically accomplished by a "muzzle-loading" technique where the fiducial 20 is placed into the distal end 19 of the needle 12 and then held in place by the bone wax plug. This can present some challenges, as the bone wax plug 22 can be visible as an artifact in the patient, potentially interfering with clear visualization of body structures or treatment devices. With this configuration, the cannula 18 must be withdrawn and reloaded after delivery of each fiducial 20. If the target locations for the fiducials are very far apart, use of a single percutaneous introducer cannula/trocar for multiple introductions of the cannula 18 may not be possible. In such a circumstance, the patient must endure several percutaneous punctures, and further endure the increased attendant risk of infection for each, including inadvertent puncturing or trauma to surrounding tissue.

In order to implant a fiducial 20 at a target location in a patient, a clinician first pushes the cannula 18 in a first direction, as indicated by arrow A, so as to insert the tip 19 into the patient (typically under fluoroscopic visualization). The clinician then pushes the second handle 13 further in the first direction to position the tip 19 at the desired depth within the patient where a fiducial 20 is to be implanted. Throughout this motion, the clinician moves the needle 12 and the stylet 14 together as a unit. At the desired depth/location, the clinician grasps the first handle 15 with one hand and the second handle 13 with the other hand. Then, the clinician holds the first handle 15 stationary while simultaneously sliding the second handle 13 back in a second direction, as indicated by arrow B, toward the first handle 15. As shown in FIG. 2, this movement causes the cannula 18 to retract over the fiducial 20 resulting in implantation of the fiducial 20 into the patient. Alternatively, the clinician may move the first handle 15 in the first direction while sliding the second handle 13 back in the second direction or holding it stationary, thereby causing the stylet 14 to push the fiducial 20 out of the cannula 18. The procedure is then repeated to place other fiducials.

As will be appreciated from the disclosed structure, after deploying one fiducial, a clinician may reload the introducer 10 from the proximal end by completely withdrawing the stylet 14, then placing another fiducial into the needle lumen and advancing it therethrough to a second location to which the distal needle tip 19 has been directed (a "breech-loading" technique). However, having to withdraw and reload takes up valuable time and complicates the procedure, potentially requiring additional personnel, whether only the stylet is withdrawn for "breech-loading" or the entire device is withdrawn for "muzzle-loading." Furthermore, due to the withdrawing and reloading of current deployment devices, multiple percutaneous punctures are subsequently required when deploying additional fiducials to the target site, which, in turn, may result in inconsistent and/or inaccurate placement of fiducials, as well as an increased risk of trauma to surrounding tissue, increasing the risk of harm to the patient. Additionally, in some anatomies, such as the liver and pancreas, the long access length and tortuous anatomy can make it difficult to deploy fiducials using the traditional stylet-push method. As such, clinicians may find it difficult to deploy multiple fiducials in an accurate and consistent manner.

SUMMARY

The present disclosure provides a deployment device configured for controlled deployment of at least one of a plurality of preloaded specially-configured fiducials in a controlled serial manner to a desired target site without requiring manual reloading after placement of each fiducial, thereby overcoming the drawbacks of current fiducial deployment systems and methods, including the traditional stylet-push method. The deployment device and specially-configured fiducials of the present disclosure provide a distinct configuration for rotational deployment of each fiducial, rather than the traditional stylet-push method, thereby providing a clinician with improved control and accuracy over the deployment of individual fiducials.

More specifically, each fiducial generally includes a pellet-like body having a groove helically formed along an outer surface thereof and the deployment device includes a deployment catheter having an internally threaded lumen configured to engage the helical groove of each fiducial so as to allow rotational loading and deployment. In particular, the internally threaded lumen of the catheter generally includes at least one protrusion helically formed along the inner surface of a portion of the lumen, wherein the protuberance is configured to correspondingly engage the groove of the fiducial. Each fiducial further includes a bore extending through a length thereof, wherein the bore is configured to receive a portion of an advancement mechanism and allow a rotational force (e.g., torque) to be applied thereto. Accordingly, upon receiving a rotational force from the advancement mechanism, the fiducial is configured to correspondingly rotate and translate along a length of the catheter by way of the threaded engagement between the helical groove on the outer surface of the fiducial body and the helical protrusion on the inner surface of the catheter lumen, thereby distally driving the fiducial out of the catheter into the desired target site.

The deployment device and specially-configured fiducials of the present disclosure overcome the drawbacks of current fiducial deployment systems and methods by providing a rotational deployment mechanism. In particular, the threaded configuration and engagement of each fiducial with the internal lumen of the deployment catheter eliminates the less accurate method of pushing a stylet distally through a catheter, as traditionally performed, thereby preventing any potential injury and/or trauma that might be caused by over extending the stylet during deployment. Furthermore, because deployment of the fiducials of the present invention are caused by rotational force, advancement of each fiducial can be controlled in a more precise manner, wherein the clinician can rotate the advancement mechanism incrementally, thereby resulting in incremental advancement of the fiducials. Accordingly, the rotational deployment mechanism of the present invention provides a more flexible, torqueable, and longer delivery system, allowing for better access to fiducial deployment sites that may otherwise be inaccessible to conventional deployment systems and methods.

The deployment device and specially-configured fiducials of the present disclosure may also improve healthcare professional safety, as a plurality of fiducials can be preloaded into the deployment catheter. Accordingly, the present invention would not require loading or preparation steps as required by current deployment systems, which may otherwise increase risk of injury to the healthcare professional and/or cause a transmission in body fluids due to unintentional piercing or needle sticking during handling. Additionally, through the use of torque assist and/or rotation counter mechanisms, the number of each fiducial placed can be reliably controlled. For example, in some embodiments, the advancement mechanism may include a deployment handle designed with a ratchet/pawl mechanism, such that fiducials can be deployed in a more controllable manner. Furthermore, fiducials of the present invention are configured to be retained within the deployment catheter in a more reliable manner and remain in a loaded position prior to deployment without requiring an additional retaining element, such as a fixative (such as bone wax), which can reduce the potential for contamination and/or particulate within a target site.

Furthermore, the helical groove along the external surface of each fiducial, as well as the internal helical protrusion of the catheter lumen may provide improved echogenicity and allow for high visibility when imaged under endoscopic and/or intravenous ultrasound technology. Additionally, the helical groove along the external surface of each fiducial is configured to more readily and safely engage with surrounding tissue upon deployment, thereby reducing the risk of fiducial migration or movement after deployment.

In certain aspects, the present disclosure provides a fiducial marker deployment system for deploying at least one fiducial marker to a desired target site. The system includes at least one fiducial marker having a body having a helical groove defined along an outer surface of the body extending along a length thereof. The system further includes a deployment catheter comprising an elongate tubular body having a lumen extending therethrough from an open proximal end to an open distal end of the body. The catheter lumen has at least one helical protrusion positioned along an inner surface of the lumen extending along a length thereof. The helical protrusion is configured to correspondingly engage the helical groove of the at least one fiducial marker. The system further includes an advancement mechanism coupled to the at least one fiducial marker and configured to advance the at least one fiducial marker along a length of the catheter lumen upon rotational movement of a shaft portion of the advancement mechanism.

In some embodiments, the at least one fiducial marker has a bore extending through a length thereof. The bore is configured to receive the shaft portion of the advancement mechanism. For example, the bore may be shaped and/or sized to allow torque to be applied to the fiducial marker upon rotational movement of the shaft portion of the advancement mechanism. The bore may have a shape including, but not limited to, a square, a rectangle, a triangle, a cross, a hexagon, and other polygonal shapes. Similarly, the shaft portion of the advancement mechanism may have a shape corresponding to the shape of the bore of the fiducial marker, so as to allow torque to be applied to the fiducial marker.

In some embodiments, the at least one fiducial marker is configured to correspondingly rotate about a longitudinal axis upon rotational movement of the shaft portion of the advancement mechanism. The at least one fiducial marker may further be configured to translate along a longitudinal axis of the catheter and in a direction towards the distal end of the catheter upon rotational movement of the shaft portion of the advancement mechanism. The at least one helical protrusion along the inner surface of the catheter lumen may be configured to releasably retain the at least one fiducial marker within the catheter lumen by way of engagement with the helical groove on the outer surface of the fiducial marker body.

In some embodiments, the distal end of the deployment catheter comprises a tip portion configured to pierce tissue for subsequent deployment of the at least one fiducial marker. Accordingly, upon puncturing the tissue site, a clinician may then rotate the advancement mechanism so as to advance deploy the fiducial marker into the desired location. In some embodiments, the at least one fiducial marker is comprised of a radio-opaque, non-ferromagnetic material, including, but not limited to, gold, platinum, palladium, iridium, tantalum, alloys thereof, and a combination of at least two thereof. In some embodiments, at least a section of the outer surface of the fiducial marker body has an enhanced echogenicity or acoustic reflection and/or at least a section of the internal surface of the catheter lumen has an enhanced echogenicity or acoustic reflection so as to enhance visibility when imaged under endoscopic and/or intravenous ultrasound technology to improve positioning and deployment of the fiducial marker.

In other aspects, the present disclosure provides a fiducial marker deployment system for deploying at least one fiducial marker to a desired target site. The system includes a deployment catheter having an elongate tubular body having a lumen extending therethrough from an open proximal end to an open distal end of the body. The catheter lumen has at least one helical protrusion positioned along an inner surface of the lumen and extending along a length thereof. The system further includes a plurality of fiducial markers disposed within the catheter lumen and aligned end-to-end in a single-file arrangement. Each fiducial marker includes a body having a helical groove defined along an outer surface of the body extending along a length thereof. The helical groove is configured to correspondingly engage the helical protrusion on the internal surface of the catheter lumen. The system further includes an advancement mechanism having a shaft portion disposed within the lumen of the catheter and coupled to each of the plurality of fiducial markers. The shaft portion is configured to distally advance each of the fiducial markers along a length of the catheter lumen upon rotational movement of the shaft portion.

In some embodiments, each fiducial marker has a bore extending through a length thereof, wherein the bore is configured to receive the shaft portion of the advancement mechanism. For example, in some embodiments, the bore is shaped and/or sized to allow torque to be applied to the fiducial marker upon rotational movement of the shaft portion of the advancement mechanism, wherein the bore shape may include, but is not limited to, a square, a rectangle, a triangle, a cross, a hexagon, and other polygonal shapes. The shaft portion of the advancement mechanism may have a shape corresponding to the shape of the bore of the fiducial marker, so as to allow torque to be applied to the fiducial marker.

In some embodiments, each fiducial marker is configured to correspondingly rotate about a longitudinal axis upon rotational movement of the shaft portion of the advancement mechanism and translate along a longitudinal axis of the catheter and in a direction towards the distal end of the catheter. Further, the at least one helical protrusion along the inner surface of the catheter lumen is configured to releasably retain each fiducial marker within the catheter lumen by way of engagement with the helical groove on the outer surface of the fiducial marker body. The distal end of the deployment catheter may include a tip portion configured to pierce tissue for subsequent deployment of the at least one fiducial marker.

DETAILED DESCRIPTION

By way of overview, the present disclosure is generally directed to a fiducial marker deployment system configured for controlled deployment of at least one of a plurality of preloaded specially-configured fiducials in a controlled serial manner to a desired target site. The deployment system generally includes a deployment device and at least one fiducial configured to be deployed to a target site within a patient via a rotational deployment method. More specifically, each fiducial generally includes a pellet-like body having a groove helically formed along an outer surface thereof and the deployment device includes a deployment catheter having an internally threaded lumen configured to engage the helical groove of each fiducial so as to allow rotational loading and deployment. In particular, the internally threaded lumen of the catheter generally includes at least one protrusion helically formed along the inner surface of a portion of the lumen, wherein the protuberance is configured to correspondingly engage the groove of the fiducial. Each fiducial further includes a bore extending through a length thereof, wherein the bore is configured to receive a portion of an advancement mechanism and allow a rotational force (e.g., torque) to be applied thereto. Accordingly, upon receiving a rotational force from the advancement mechanism, the fiducial is configured to correspondingly rotate and translate along a length of the catheter by way of the threaded engagement between the helical groove on the outer surface of the fiducial body and the helical protrusion on the inner surface of the catheter lumen, thereby distally driving the fiducial out of the catheter into the desired target site.

The deployment device and specially-configured fiducials of the present disclosure overcome the drawbacks of current fiducial deployment systems and methods by providing a rotational deployment mechanism. In particular, the threaded configuration and engagement of each fiducial with the internal lumen of the deployment catheter eliminates the less accurate method of pushing a stylet distally through a catheter, as traditionally performed, thereby preventing any potential injury and/or trauma that might be caused by over extending the stylet during deployment. Furthermore, because deployment of the fiducials of the present invention are caused by rotational force, advancement of each fiducial can be controlled in a more precise manner, wherein the clinician can rotate the advancement mechanism incrementally, thereby resulting in incremental advancement of the fiducials. Accordingly, the rotational deployment mechanism of the present invention provides a more flexible, torqueable, and longer delivery system, allowing for better access to fiducial deployment sites that may otherwise be inaccessible to conventional deployment systems and methods.

The deployment device and specially-configured fiducials of the present disclosure may also improve healthcare professional safety, as a plurality of fiducials can be preloaded into the deployment catheter. Accordingly, the present invention would not require loading or preparation steps as required by current deployment systems, which may otherwise increase risk of injury to the healthcare professional and/or cause a transmission in body fluids due to unintentional piercing or needle sticking during handling. Additionally, through the use of torque assist and/or rotation counter mechanisms, the number of each fiducial placed can be reliably controlled. For example, in some embodiments, the advancement mechanism may include a deployment handle designed with a ratchet/pawl mechanism, such that fiducials can be deployed in a more controllable manner. Furthermore, fiducials of the present invention are configured to be retained within the deployment catheter in a more reliable manner and remain in a loaded position prior to deployment without requiring an additional retaining element, such as a fixative (such as bone wax), which can reduce the potential for contamination and/or particulate within a target site.

Furthermore, the helical groove along the external surface of each fiducial, as well as the internal helical protrusion of the catheter lumen may provide improved echogenicity and allow for high visibility when imaged under endoscopic and/or intravenous ultrasound technology. Additionally, the helical groove along the external surface of each fiducial is configured to more readily and safely engage with surrounding tissue upon deployment, thereby reducing the risk of fiducial migration or movement after deployment.

Figure 3:
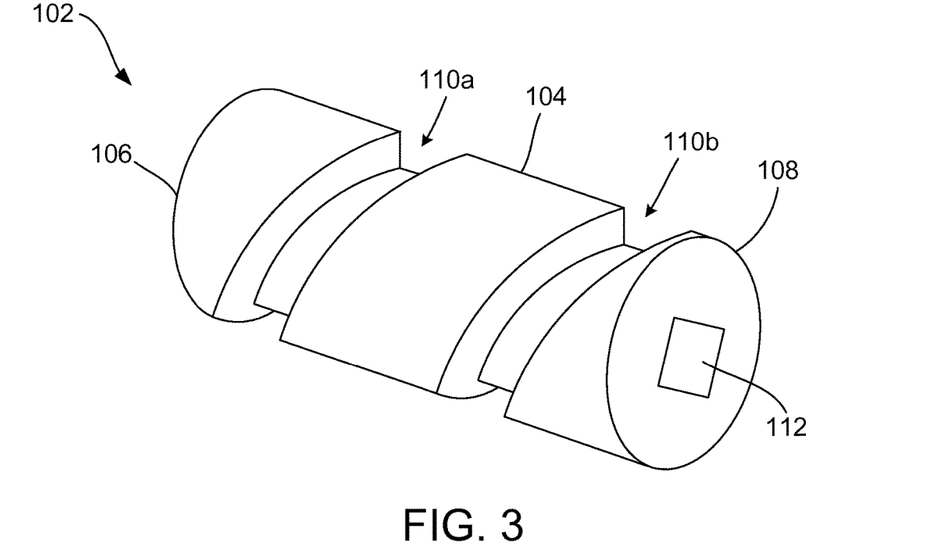
FIG. 3 is a perspective view of a fiducial marker consistent with the present disclosure.
Figure 4:
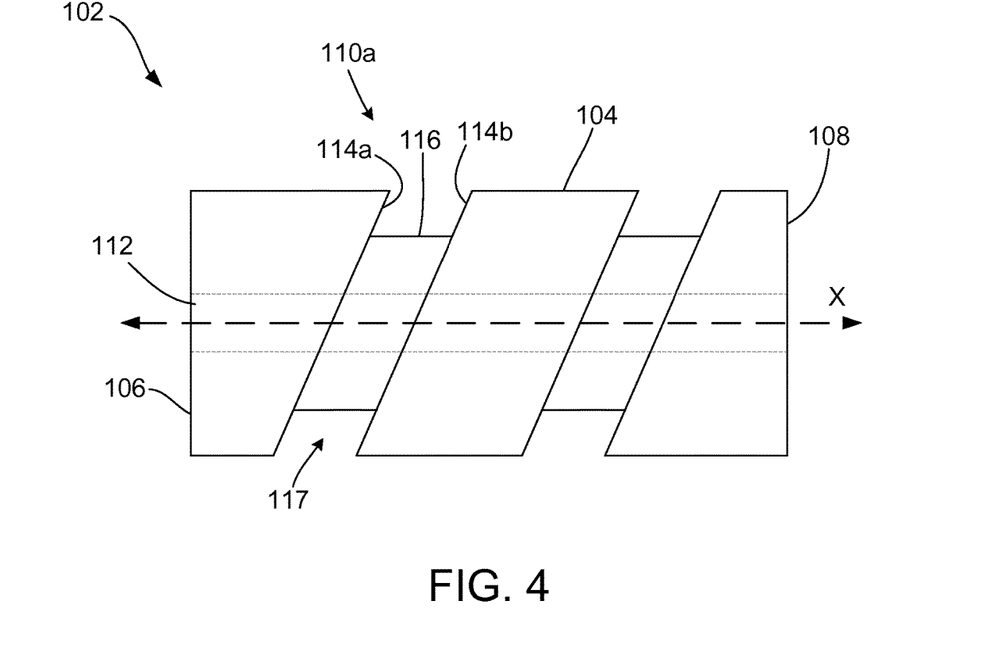
FIG. 4 is a side view of the fiducial marker of FIG. 3.

FIG. 3 is a perspective view of a fiducial marker 102 consistent with the present disclosure and FIG. 4 is a side view of the fiducial marker 102 of FIG. 3. As shown, the fiducial marker 102 (hereinafter referred to as "fiducial") generally includes a body 104 having a first end 106 and an opposing second end 108. In the illustrated embodiment, the fiducial 102 is shown in a pellet-like form. However, it should be noted that the fiducial body 102 may take a variety of shapes as generally understood by one skilled in the art, particularly depending on the specific application/procedure and/or target site to which the fiducial 102 is to be deployed.

In the illustrated embodiment, the fiducial 102 includes a helical groove 110 defined along an outer surface of the body 104 and generally extending along the length of the body 104 from the first to the second ends 106, 108. The helical groove 110 may generally revolve about the outer surface of the body 104 relative to a longitudinal axis X of the fiducial body 104. As shown, at least two portions 110a, 110b of the groove 110 can be seen on the fiducial body 104, formed from the groove 110 extending along the outer surface for at least one complete revolution about the fiducial body 104. Depending on the size, length, and other dimensions, the groove 110 may have more or less revolutions about the fiducial body 104, thus resulting in more or less portions. As shown in FIG. 4, the groove 110 may generally be continuous and include at least opposing sidewalls 114a, 114b extending from the outer surface towards the center of the fiducial 102 and terminating at a base wall 116, thereby forming a clearance or void 117 there between. As described in greater detail herein, the clearance 117 of the groove 110 is shaped and/or sized to engage a protrusion formed along an inner surface of a lumen of a deployment catheter, thereby allowing rotational deployment of the fiducial 102. The fiducial 102 further includes a bore 112 extending through a length thereof, wherein the bore 112 is configured to receive a portion (e.g., shaft) of an advancement mechanism, as described in greater detail herein.

The fiducial 102 (and other fiducial embodiments described herein) may be formed of a radio-opaque, non-ferromagnetic material including, but not limited to, gold, platinum, palladium, iridium, tantalum, alloys thereof, and combinations thereof. Having a radio-opaque characteristic will allow the fiducial 102 to be used in deployment techniques using fluoroscopy, as well as making it detectable/visualized by radiographic means during a treatment or other procedure where it may be desirable to know the location(s) of one or more fiducials. Being non-ferromagnetic will lessen the likelihood that visualization techniques or other procedures employing magnetic fields such as, for example, MRI, will re-orient or otherwise dislodge a fiducial. Furthermore, echogenic construction of a fiducial 102 may be enhanced by surface texture, but can also be provided by structural inclusions such as embedded bubbles or beads that provide for a different ultrasound reflectivity than material surrounding them. Furthermore, inclusion of the helical groove 110 along the fiducial body 104 may further enhance echogenicity and allow for high visibility when imaged under endoscopic and/or intravenous ultrasound technology.

Fiducials consistent with the present disclosure may also be coated with a material configured to reduce backscatter during radiography.

Figure 5:
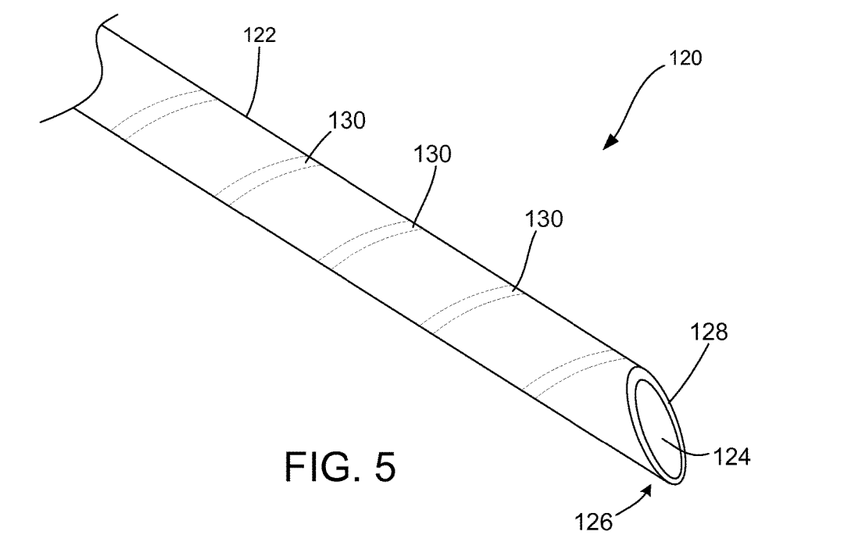
FIG. 5 is a perspective view of a deployment catheter configured for deployment of the fiducial markers consistent with the present disclosure.
Figure 6:
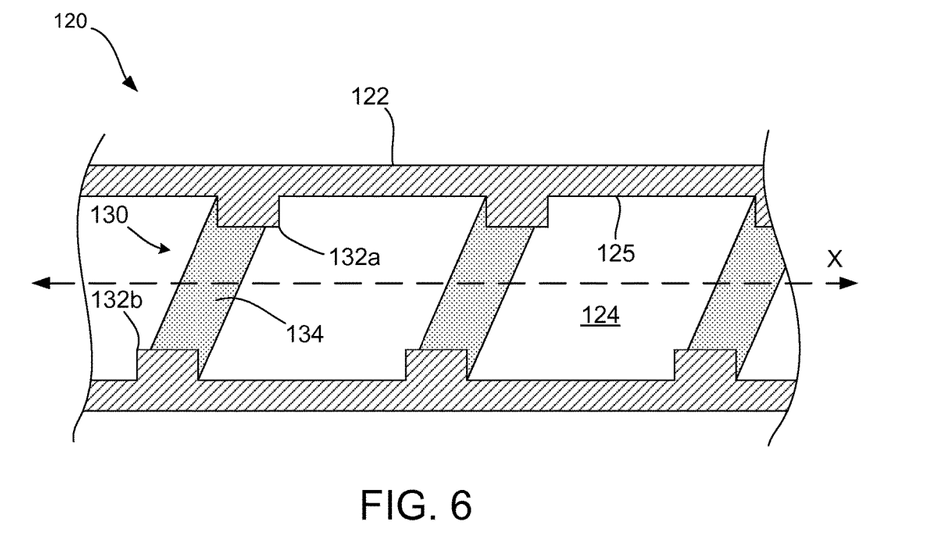
FIG. 6 is a cross-sectional side view of the deployment catheter of FIG. 5.

FIG. 5 is a perspective view of a deployment catheter 120 configured for deployment of a fiducial marker consistent with the present disclosure, such as the fiducial 102 of FIGS. 3 and 4. FIG. 6 is a cross-sectional side view of the deployment catheter 120. As shown, the deployment catheter 120 generally includes an elongate tubular body 122 having a lumen 124 extending therethrough from an open proximal end (not shown) to an open distal end 126 of the body. The distal end 126 generally includes a pointed distal tip 128 configured to engage and pierce tissue to allow subsequent deployment of fiducial therefrom. As shown, the lumen 124 includes internal threading 130 helically formed along an interior surface 125 thereof. In particular, as shown in FIG. 6, the threading 130 may include a protrusion 132 helically formed along an interior surface 125 of the lumen 124 and generally extending along a length of the catheter body 122, similar to the appearance of the rifling on a barrel for a firearm. The helical protrusion 132 may generally revolve about the internal surface 125 of the catheter lumen 124 relative to a longitudinal axis X of the catheter body 122. As shown, the protrusion may have a first portion 132a and a second portion 132b generally opposing one another along a cross section of the catheter body 122, thereby illustrating the helical nature of the protrusion. As shown, the protrusion 132 may generally be continuous (as indicated by portion 134 continuously rotating along the inner surface 125). The helical protrusion 132 is shaped and/or sized to correspondingly engage the helical groove 110 of the fiducial marker 102, such that the protrusion is configured to be received within the clearance 117 of the groove 110 and releasably retain the fiducial 102 within the catheter lumen 124 along a length of the catheter body 122.

As generally understood, the catheter 120 itself can be manufactured from a variety of metallic based materials, including, but not limited to, nitinol, cobalt chrome, stainless steel, a metal alloy, combinations thereof, nanotube composites, including materials such as carbon, silicon, boron nitride, inorganic materials, or combinations thereof, or polymeric based materials including, but not limited to poly-ether-ether ketone, polyamide, polyethersulfone, polyurethane, ether block amide copolymers, polyacetal, polytetrafluoroethylene and/or derivatives thereof. It should be noted that the catheter 120 is not limited to any particular gauge (e.g., outer diameter). For example, depending on the type of fiducial to be deployed, as well as the target site in which deployment is to occur, the deployment catheter 120 may range from 10-gauge to 40-gauge, and more specifically 15-gauge to 28-gauge, i.e., gauge 12, 14, 15, 16, 17, 18, 19, 20, 21, 22, 23, 24, or 25 catheters.

Furthermore, similar to the fiducial 102, echogenic construction of a catheter 120 may be enhanced by surface texture, particularly at or near the distal end 126, but can also be provided by structural inclusions such as embedded bubbles or beads that provide for a different ultrasound reflectivity than material surrounding the catheter. Furthermore, inclusion of the internal threading 130 may further enhance echogenicity and allow for high visibility when imaged under endoscopic and/or intravenous ultrasound technology. Catheters consistent with the present disclosure may also be coated with a material configured to reduce backscatter during radiography.

Figure 7:
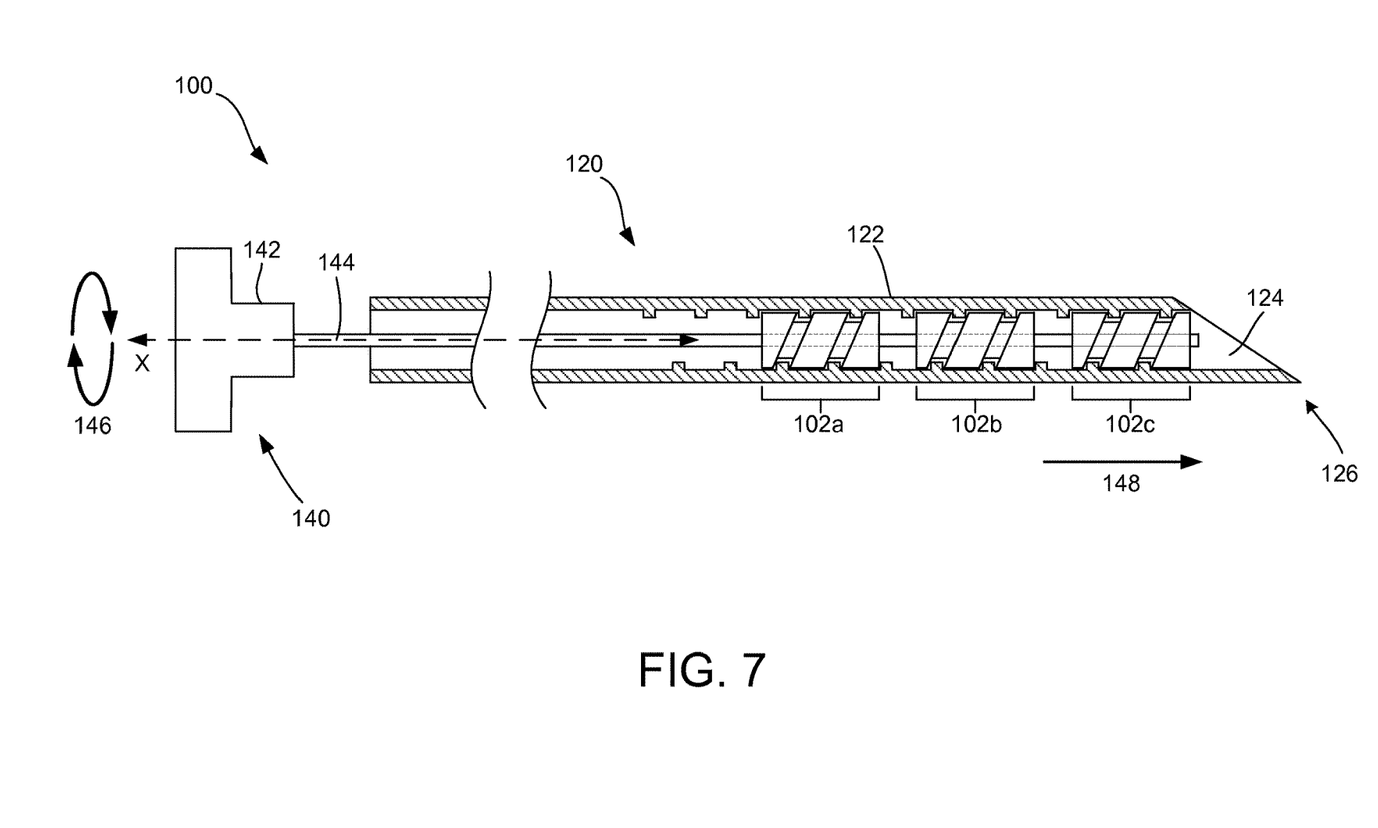
FIG. 7 is a side view, partly in section, of a deployment system consistent with the present disclosure illustrating a plurality of fiducials preloaded within the deployment catheter.

FIG. 7 is a side view, partly in section, of a deployment system 100 consistent with the present disclosure illustrating a plurality of fiducials 102a-102c preloaded within the deployment catheter 120. As shown, a plurality of fiducials 102a, 102b, 102c may be preloaded within the deployment catheter 120 of the present invention. As shown, the helical groove of each fiducial correspondingly engages the helical protrusion formed along the inner surface of the catheter lumen 124, thereby retaining the fiducials 102a-102c within the catheter lumen 124 in a loaded position. In the illustrated embodiment, the fiducials 102a-102c are loaded and aligned end-to-end in a single-file arrangement, which allows each fiducial to be individually deployed in a controlled serial fashion, as described in greater detail herein.

Figure 9:
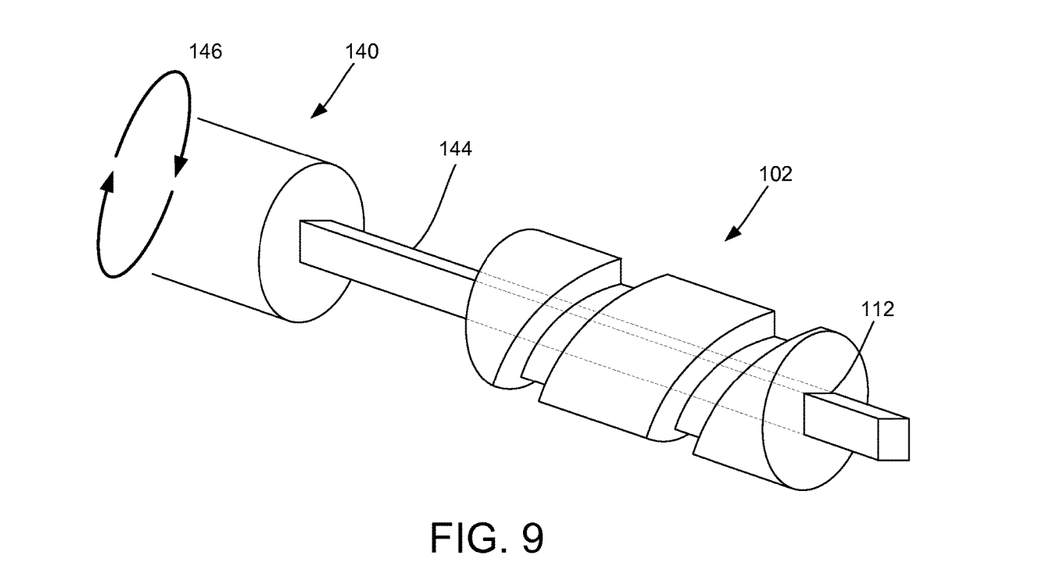
FIG. 9 is an enlarged perspective view of the advancement mechanism of the system of FIG. 7 coupled to at least one fiducial marker consistent with the present disclosure.

As shown, the system 100 further includes an advancement mechanism 140 coupled to each of the fiducials 102a-102c by way of the bore 112 of each fiducial 102 (shown in FIG. 9). In the illustrated embodiment, the advancement mechanism 140 is in the form of a mandrel having a handle portion 142 and a shaft portion 144 extending therefrom. The shaft 144 generally extends from the proximal end to the distal end 126 of the catheter body 126 and is coupled to each fiducial 102 within the catheter lumen 126.

During deployment, the clinician is able to first select a target site and percutaneously puncture the target site via the pointed distal tip 128 of the distal end 126 of the catheter 120 so as to gain access to the target site for deployment of the one or more fiducials 102a-102c. In order to advance at least fiducial 102c out of the catheter 120 for deployment, the clinician need rotate the handle 142 of the mandrel 140, which in turn rotates the shaft portion about a longitudinal axis X, as indicated by arrow 146. Each of the fiducials 102a-102c are configured to correspondingly rotate about a longitudinal axis X upon rotational movement of the shaft portion 144. In turn, due in part to the engagement between the helical groove of each fiducial and the helical protrusion of the catheter lumen, each fiducial 102 is configured to translate along a length of the catheter 120 and in a direction towards the distal end 126 of the catheter, as indicated by arrow 148, upon rotational movement of the shaft portion 144. In other words, rotation of the advancement mechanism 140 generally results in a screw-like translation of the fiducials so as to deploy the fiducials in a controlled and accurate manner and generally requires less force for deployment when compared to the traditional stylet-push method, which relies only on a distal lateral force.

Additionally, through the use of torque assist and/or rotation counter mechanisms, the number fiducials to be placed can be reliably controlled. For example, in some embodiments, the advancement mechanism may include a deployment handle designed with a ratchet/pawl mechanism, such that fiducials can be deployed in a more controllable manner. Accordingly, the advancement mechanism 140 may include some form of a ratcheting handle which, upon depression, may cause incremental rotation of the shaft 144, resulting in a more controlled deployment of fiducials.

Figure 8:
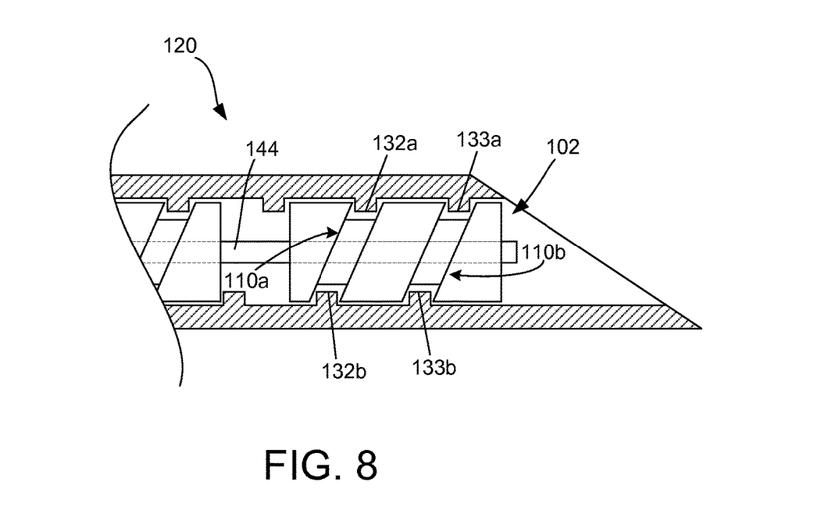
FIG. 8 is an enlarged side view, partly in section, of a portion of the deployment catheter having fiducials loaded within.

FIG. 8 is an enlarged side view, partly in section, of a portion of the deployment catheter 120 of FIG. 7. As shown, the at least two portions 110a, 110b of the groove 110 of fiducial 102 are shaped and/or sized to receive portions 132a-132b and 133a-133b of the helical protrusion of the interior surface 125 of the catheter lumen 124. Accordingly, the helical protrusion is configured to releasably retain the fiducial 102 within the catheter lumen 124 by way of the helical groove and helical protrusion engagement, particularly resisting movement in a lateral direction, absent rotation of the fiducial 102 and/or the catheter body 122 itself. Accordingly, lateral movement of the fiducial 102 is generally restricted to rotation of the shaft portion 144 of the mandrel 140, thereby providing a clinician within improved control over fiducial movement and deployment.

Figure 10A:
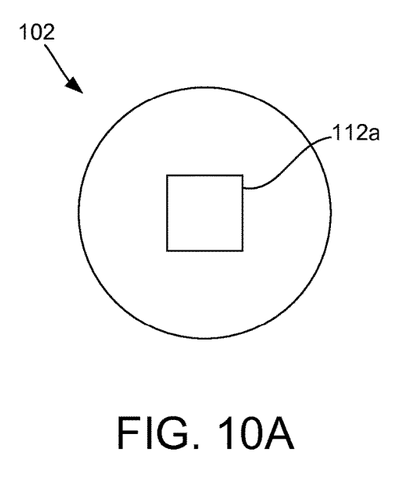
FIGS. 10A-10D are end views of fiducial markers consistent with the present disclosure illustrating different bore shapes/contours.
Figure 10B:
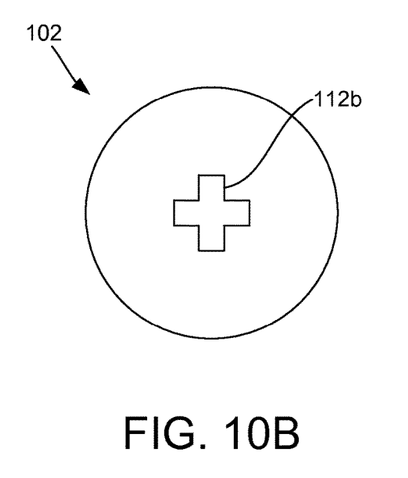
Figure 10C:
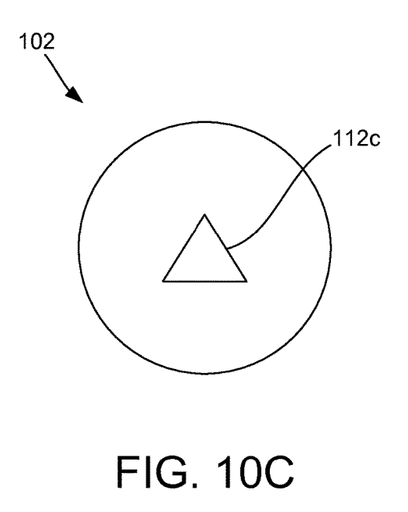
Figure 10D:
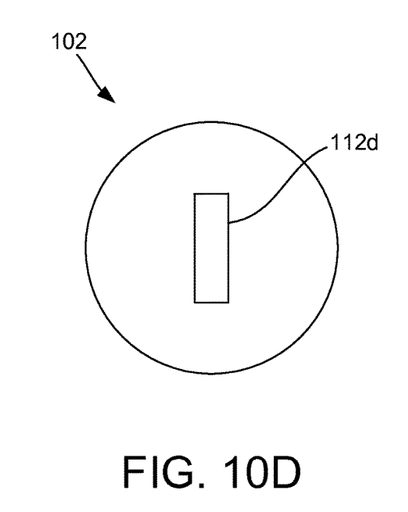

FIG. 9 is an enlarged perspective view of the advancement mechanism 140 of the system 100 of FIG. 7 coupled to at least one fiducial 102 consistent with the present disclosure. As previously described, a fiducial 102 includes a bore extending through a length thereof, wherein the bore is configured to receive the shaft portion 144 of the advancement mechanism 140. As shown, the bore 112 is shaped and/or sized to allow torque to be applied to the fiducial 102 upon rotational movement, as indicated by arrow 146, of the shaft portion 144. Accordingly, the bore 112 generally has a shape selected from the group consisting of: a square, a rectangle, a triangle, a cross, a hexagon, and other polygonal shapes. In the illustrated embodiment, the bore 112 has a square shape. In turn, the shaft portion 144 has a shape that generally corresponds to the shape of the bore 112. In this instance, the shaft portion 144 has a square shape. FIGS. 10A-10D are end views of fiducial 102 consistent with the present disclosure illustrating different bore 112 shapes/contours. FIG. 10A illustrates a square shape. FIG. 10B illustrates a cross shape. FIG. 10C illustrates a triangle shape. FIG. 10D illustrates a rectangular slotted shape. In any event, the bore 112 generally includes a shape configured to allow a torque force to be applied to the fiducial so as to allow the fiducial to rotate and advance along a length of the catheter for deployment. Accordingly, certain shapes would not be ideal, such as a circular shape.

The deployment device and specially-configured fiducials of the present disclosure overcome the drawbacks of current fiducial deployment systems and methods by providing a rotational deployment mechanism. In particular, the threaded configuration and engagement of each fiducial with the internal lumen of the deployment catheter eliminates the less accurate method of pushing a stylet distally through a catheter, as traditionally performed, thereby preventing any potential injury and/or trauma that might be caused by over extending the stylet during deployment. Furthermore, because deployment of the fiducials of the present invention are caused by rotational force, advancement of each fiducial can be controlled in a more precise manner, wherein the clinician can rotate the advancement mechanism incrementally, thereby resulting in incremental advancement of the fiducials. Accordingly, the rotational deployment mechanism of the present invention provides a more flexible, torqueable, and longer delivery system, allowing for better access to fiducial deployment sites that may otherwise be inaccessible to conventional deployment systems and methods.

The deployment device and specially-configured fiducials of the present disclosure may also improve healthcare professional safety, as a plurality of fiducials can be preloaded into the deployment catheter. Accordingly, the present invention would not require loading or preparation steps as required by current deployment systems, which may otherwise increase risk of injury to the healthcare professional and/or cause a transmission in body fluids due to unintentional piercing or needle sticking during handling. Additionally, through the use of torque assist and/or rotation counter mechanisms, the number of each fiducial placed can be reliably controlled. For example, in some embodiments, the advancement mechanism may include a deployment handle designed with a ratchet/pawl mechanism, such that fiducials can be deployed in a more controllable manner. Furthermore, fiducials of the present invention are configured to be retained within the deployment catheter in a more reliable manner and remain in a loaded position prior to deployment without requiring an additional retaining element, such as a fixative (such as bone wax), which can reduce the potential for contamination and/or particulate within a target site.

Furthermore, the helical groove along the external surface of each fiducial, as well as the internal helical protrusion of the catheter lumen may provide improved echogenicity and allow for high visibility when imaged under endoscopic and/or intravenous ultrasound technology. Additionally, the helical groove along the external surface of each fiducial is configured to more readily and safely engage with surrounding tissue upon deployment, thereby reducing the risk of fiducial migration or movement after deployment.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A fiducial marker deployment system comprising:
   at least one fiducial marker having a helical groove defined along an outer surface of the fiducial marker extending along a length thereof, wherein the at least one fiducial marker has a bore extending through a length thereof;
   a deployment catheter comprising an elongate tubular body having a lumen extending therethrough from an open proximal end to an open distal end of the elongate tubular body, the lumen having at least one helical protrusion formed along an inner surface of the lumen and extending along a length thereof, the at least one helical protrusion configured to releasably retain the at least one fiducial marker within the lumen by correspondingly engaging the helical groove of the at least one fiducial marker; and
   an advancement mechanism extending through the lumen and configured to rotate the at least one fiducial marker with respect to the lumen along the at least one helical protrusion of the lumen to advance the at least one fiducial marker along a length of the lumen upon rotational movement of a shaft portion of the advancement mechanism, wherein the bore of the at least one fiducial marker is configured to receive the shaft portion of the advancement mechanism.

2. The fiducial marker deployment system of claim 1, wherein the bore is shaped, or sized, or both, to allow torque to be applied to the fiducial marker upon rotational movement of the shaft portion of the advancement mechanism.

3. The fiducial marker deployment system of claim 2, wherein the bore has a shape selected from a group consisting of: a square, a rectangle, a triangle, a cross, a hexagon, and other polygonal shapes.

4. The fiducial marker deployment system of claim 3, wherein the shaft portion of the advancement mechanism has a shape corresponding to the shape of the bore of the fiducial marker.

5. The fiducial marker deployment system of claim 1, wherein the at least one fiducial marker is configured to correspondingly rotate about a longitudinal axis upon rotational movement of the shaft portion of the advancement mechanism.

6. The fiducial marker deployment system of claim 1, wherein the at least one fiducial marker is configured to translate along a longitudinal axis of the deployment catheter and in a direction towards a distal end of the deployment catheter upon rotational movement of the shaft portion of the advancement mechanism.

7. The fiducial marker deployment system of claim 1, wherein a distal end of the deployment catheter comprises a tip portion configured to pierce tissue for subsequent deployment of the at least one fiducial marker.

8. The fiducial marker deployment system of claim 1, wherein the at least one fiducial marker is comprised of a radio-opaque, non-ferromagnetic material.

9. The fiducial marker deployment system of claim 8, wherein the at least one fiducial marker is comprised of a material selected from a group consisting of: gold, platinum, palladium, iridium, tantalum, alloys thereof, and a combination of at least two thereof.

10. The fiducial marker deployment system of claim 1, wherein at least a section of the outer surface of the fiducial marker has an enhanced echogenicity or acoustic reflection with respect to another section of the outer surface of the fiducial marker.

11. The fiducial marker deployment system of claim 1, wherein at least a section of the inner surface of the lumen has an enhanced echogenicity or acoustic reflection with respect to another section of the inner surface of the lumen.

12. The fiducial marker deployment system of claim 1, wherein a distal end of the deployment catheter comprises a tip portion configured to pierce tissue for subsequent deployment of the at least one fiducial marker.

13. A fiducial marker deployment system comprising:
   a deployment catheter comprising an elongate tubular body having a lumen extending therethrough from an open proximal end to an open distal end of the elongate tubular body, the lumen having at least one helical protrusion formed along an inner surface of the lumen and extending along a length thereof;
   a plurality of fiducial markers disposed within the lumen and aligned end-to-end in a single-file arrangement, each fiducial marker having a bore extending through a length thereof, each fiducial marker having a helical groove defined along an outer surface of each fiducial marker extending along a length thereof, the helical groove configured to releasably retain the plurality of fiducial markers within the lumen by correspondingly engaging the at least one helical protrusion on the inner surface of the lumen; and
   an advancement mechanism having a shaft portion extending through the lumen of the deployment catheter and coupled to each of the plurality of fiducial markers, the shaft portion configured to rotate the plurality of fiducial markers with respect to the lumen along the at least one helical protrusion of the lumen to distally advance each of the plurality of fiducial markers along a length of the lumen upon rotational movement of the shaft portion, wherein the bore of the plurality of fiducial markers is configured to receive the shaft portion of the advancement mechanism.

14. The fiducial marker deployment system of claim 13, wherein the bore is shaped, or sized, or both, to allow torque to be applied to the fiducial marker upon rotational movement of the shaft portion of the advancement mechanism, the bore has a shape selected from a group consisting of: a square, a rectangle, a triangle, a cross, a hexagon, and other polygonal shapes.

15. The fiducial marker deployment system of claim 14, wherein the shaft portion of the advancement mechanism has a shape corresponding to the shape of the bore of the fiducial marker.

16. The fiducial marker deployment system of claim 13, wherein each fiducial marker is configured to correspondingly rotate about a longitudinal axis upon rotational movement of the shaft portion of the advancement mechanism and translate along a longitudinal axis of the deployment catheter and in a direction towards a distal end of the deployment catheter.

* * * * *